United States Patent
Guo et al.

(10) Patent No.: US 11,479,663 B2
(45) Date of Patent: Oct. 25, 2022

(54) POLYOLEFIN COMPOSITION

(71) Applicant: SABIC GLOBAL TECHNOLOGIES B.V., Bergen Op Zoom (NL)

(72) Inventors: Jing Guo, Pudong (CN); Xiqiang Liu, Pudong (CN); Chaodong Jiang, Pudong (CN); Shengying Qian, Pudong (CN); Chunfa Li, Pudong (CN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 254 days.

(21) Appl. No.: 16/616,776

(22) PCT Filed: Jul. 30, 2018

(86) PCT No.: PCT/EP2018/070611
§ 371 (c)(1),
(2) Date: Nov. 25, 2019

(87) PCT Pub. No.: WO2019/025372
PCT Pub. Date: Feb. 7, 2019

(65) Prior Publication Data
US 2021/0301115 A1 Sep. 30, 2021

(30) Foreign Application Priority Data
Jul. 31, 2017 (EP) .................................... 17183922

(51) Int. Cl.
| C08L 23/16 | (2006.01) |
| A61L 29/04 | (2006.01) |
| A61L 29/14 | (2006.01) |
| C08J 5/18 | (2006.01) |
| A61J 1/10 | (2006.01) |

(52) U.S. Cl.
CPC ............. *C08L 23/16* (2013.01); *A61L 29/041* (2013.01); *A61L 29/14* (2013.01); *C08J 5/18* (2013.01); *A61J 1/10* (2013.01); *C08J 2323/16* (2013.01); *C08J 2423/08* (2013.01); *C08J 2423/14* (2013.01); *C08L 2201/08* (2013.01); *C08L 2203/16* (2013.01); *C08L 2205/025* (2013.01); *C08L 2205/03* (2013.01)

(58) Field of Classification Search
CPC ........... C08L 2205/03; C08L 2205/035; C08L 2205/025; C08L 23/0815; C08L 23/12
See application file for complete search history.

(56) References Cited

U.S. PATENT DOCUMENTS

| 6,630,544 | B1 * | 10/2003 | Klendworth | C08F 10/06 502/103 |
| 2002/0035210 | A1 | 3/2002 | Silvestri et al. | |
| 2007/0251572 | A1 * | 11/2007 | Hoya | B32B 27/32 136/256 |
| 2013/0253125 | A1 * | 9/2013 | Kock | C08L 23/12 524/528 |

FOREIGN PATENT DOCUMENTS

| EP | 0557953 A1 | 9/1993 |
| EP | 1820821 A1 | 8/2007 |
| WO | 2009077293 A1 | 6/2009 |

OTHER PUBLICATIONS

International Search Report; International Application No. PCT/EP2018/070611; International Filing Date: Jul. 30, 2018; dated Sep. 20, 2018; 3 pages.
Written Opinion; International Application No. PCT/EP2018/070611; International Filing Date: Jul. 30, 2018; dated Sep. 20, 2018; 5 pages.

* cited by examiner

Primary Examiner — Jeffrey C Mullis
(74) Attorney, Agent, or Firm — Cantor Colburn LLP

(57) ABSTRACT

The invention relates to a composition comprising: (A) a propylene-based polymer which is a propylene homopolymer or a propylene copolymer consisting of at least 90 wt % of propylene monomer units and at most 10 wt % of ethylene monomer units and/or an α-olefin monomer units having 4 to 10 carbon atoms, (B) a terpolymer of propylene, an α-olefin having 4 to 10 carbon atoms and ethylene and (C) a copolymer of ethylene and an α-olefin having 4 to 10 carbon atoms, wherein the copolymer (C) has a density of at least 0.880 g/cm$^3$, wherein the amount of the propylene-based polymer (A) is at least 60 wt % with respect to the total composition.

20 Claims, No Drawings

POLYOLEFIN COMPOSITION

CROSS REFERENCE TO RELATED APPLICATIONS

This application is a 371 of International Application No. PCT/EP2018/070611, filed Jul. 30, 2018, which is incorporated by reference in its entirety, and which claims priority to European Application Serial No. 17183922.8, filed Jul. 31, 2017.

The present invention relates to a polyolefin composition and an article comprising such polyolefin composition.

It is known in the art to modify the mechanical properties of polypropylene such as the flexibility and the impact resistance by adding a certain quantity of elastomeric olefin copolymer to the polypropylene, such as ethylene-propylene rubber (EPR). However, since the refraction index of EPR is different from that of polypropylene, the resulting compositions are usually opaque. This limits the application of such compositions as most (film/packaging) applications require more transparency.

To overcome such problem it has been proposed, as disclosed in EP-A-0557953, to add certain amounts of ethylene polymers to the said blends of polypropylene and elastomeric olefin copolymers.

WO2009077293 discloses a transparent polyolefin composition comprising a propylene homopolymer or copolymer and a butene-1/ethylene copolymer.

US2002035210 discloses an elastomeric thermoplastic polyolefin composition comprising 1-55 wt % of a crystalline propylene polymer, 1-55 wt % of an atactic or amorphous propylene polymer and 1-55 wt % of an elastomeric olefin polymer consisting of copolymers of ethylene with C3-C8 comonomer.

Further, packaging applications are important for polyolefin compositions, also in the medical area and for pharmaceutical packaging where the material is mostly sterilised. Especially in food packaging and medical applications, films made of or essentially consisting of propylene random copolymers have to be sterilised. The most common sterilisation procedures are the use of heat (steam), radiation (beta radiation, electrons or gamma radiation) or chemicals (usually ethylene oxide). This sterilisation procedure affects the mechanical and optical properties, but sometimes also the organoleptic properties of the material significantly.

Steam sterilisation, usually carried out in a temperature range of 120 to 130° C., results mostly in post-crystallisation and physical ageing effects of the polypropylene. Moreover, the material tends to become stiffer and more brittle. Also optical disturbances are severely increased and significantly increase the haze of transparent articles.

Especially in steam sterilisation, performed at 121° C. for 30 min, the crystallinity of films made of alpha-olefin copolymers significantly increases, resulting in a modulus and haze increase together with significant embrittlement. Thus, a reduction of the impact strength is further observed. To overcome the above drawbacks, it has been tried to increase the homogeneity of monomer incorporation into the polymer chain of a propylene copolymer. In the field of packaging, propylene-ethylene random copolymers have gained increasing interest due to their improved transparency, relative softness, lower sealing temperature and moderate low-temperature impact strength. Nevertheless, the incorporation of comonomers into the propylene polymer chain concentrates stereo defects into the polymer chains, which in turn are leading to intermolecular heterogeneity of the propylene copolymer. Such heterogeneity increases the above outlined drawbacks, especially after performing sterilisation on films made of such propylene copolymer compositions.

While known compositions may have optical and mechanical properties which are satisfactory in some applications, there is still need in the art for a polyolefin composition having a combination of good optical properties and good mechanical properties.

It is an object of the present invention to provide a polyolefin composition having a combination of good optical properties and good mechanical properties.

Accordingly, the present invention provides a composition comprising:

(A) a propylene-based polymer which is a propylene homopolymer or a propylene copolymer consisting of at least 90 wt % of propylene monomer units and at most 10 wt % of ethylene monomer units and/or an α-olefin monomer units having 4 to 10 carbon atoms, (B) a terpolymer of propylene, an α-olefin having 4 to 10 carbon atoms and ethylene and (C) a copolymer of ethylene and an α-olefin having 4 to 10 carbon atoms, wherein the amount of the propylene-based polymer (A) is at least 60 wt % with respect to the total composition.

It was found that the composition according to the invention has a combination of good optical properties and good mechanical properties.

In addition, an advantage of the composition of the invention may be that it can suitably be used for medical applications, especially for medical applications wherein the packaging needs to be steam sterilized.

(A) Propylene-Based Polymer

The composition according to the invention comprises (A) a propylene-based polymer. The propylene-based polymer may be a propylene homopolymer or a propylene copolymer with at most 10 wt % of comonomer units. The comonomer units may be ethylene monomer units and/or an α-olefin monomer units having 4 to 10 carbon atoms.

Preferably, the propylene-based polymer is a random propylene-ethylene copolymer consisting of 90 to 99 wt % of propylene monomer units and 1 to 10 wt % of ethylene monomer units.

Preferably, the propylene-based polymer has a melt flow rate of from 1 to 30 dg/min, for example 2 to 20 dg/min or 5 to 10 dg/min, as measured according to ISO1133 (2.16 kg, 230° C.).

Preferably, the propylene-based polymer has a xylene soluble content at 25° C. of 4 to 10 wt %.

The amount of the propylene-based polymer in the composition is at least 60 wt %, preferably 60 to 98 wt % or 60 to 90 wt %, for example 60 to 75 wt % or 75 to 90 wt %, with respect to the total composition (100 wt %).

(B) Terpolymer of Propylene, an α-olefin Having 4 to 10 Carbon Atoms and Ethylene The composition according to the invention comprises (B) a terpolymer of propylene, an α-olefin having 4 to 10 carbon atoms and ethylene. Preferably, the terpolymer (B) is a terpolymer of propylene, 1-butene and ethylene.

Preferably, the amount of propylene in the terpolymer (B) is 70 to 90 wt % with respect to the terpolymer (B).

Preferably, the amount of the α-olefin in the terpolymer (B) is 5 to 30 wt % with respect to the terpolymer (B). More preferably, the amount of the α-olefin in the terpolymer (B) is 15 to 30 wt % with respect to the terpolymer (B). This results in a lower haze of the composition according to the invention.

Preferably, the amount of ethylene in the terpolymer (B) is 1 to 10 wt % with respect to the terpolymer (B).

Preferably, the terpolymer has a melt flow rate of from 1 to 35 dg/min or 2 to 30 dg/min, for example 2 to 15 dg/min or 15 to 30 dg/min, as measured according to ISO1133 (2.16 kg, 230° C.).

Preferably, the amount of the terpolymer (B) in the composition is 1 to 30 wt % or 5 to 20 wt % with respect to the total composition.

(C) Copolymer of Ethylene and an α-olefin Having 4 to 10 Carbon Atoms

The composition according to the invention comprises (C) a copolymer of propylene and an α-olefin having 4 to 10 carbon atoms. Preferably, the copolymer (C) is a copolymer of propylene and 1-butene.

Preferably, the copolymer (C) has a density of 0.850 to 0.900 g/cm$^3$.

In some embodiments, the copolymer (C) has a density of at least 0.880 g/cm$^3$. This results in a lower haze of the composition according to the invention.

In some embodiments, the copolymer (C) has a density of less than 0.880 g/cm$^3$. This results in a high impact strength of the composition according to the invention.

Preferably, the copolymer (C) has a melt flow rate of from 1 to 15 dg/min as measured according to ISO1133 (2.16 kg, 230° C.).

Preferably, the amount of the copolymer (C) in the composition is 1 to 30 wt % or 5 to 20 wt % with respect to the total composition.

Preferably, the total amount of the terpolymer (B) and the copolymer (C) is 15 to 40 wt %% with respect to the total composition.

Preferably, the weight ratio of the terpolymer (B) to the copolymer (C) is 0.5 to 4, preferably 1 to 3.5.

Preferably, the total of (A), (B) and (C) is at least 95 wt %, at least 98 wt %, at least 99 wt %, at least 99.5 wt %, at least 99.9 wt % or 100 wt % of the total composition.

(D) Additives

The composition may further comprise (D) additives, wherein the total of (A), (B), (C) and (D) is 100 wt % of the total composition. Preferably, the amount of (D) is up to 5000 ppm, more preferably at most 4000 ppm, more preferably at most 3000 ppm, more preferably at most 2500 ppm, more preferably at most 2000 ppm, more preferably at most 1500 ppm, for example at most 1000 ppm or at most 500 ppm, of the total composition. Typically, the amount of (D) is at least 500 ppm of the total composition. The additives may contain commonly used additives like: phenolic antioxidants phosphorus-containing antioxidants, C-radical scavengers, acid scavengers, UV-stabilisers, antistatic agents, nucleating agents, slip agents, and antiblocking agents. These components are well known for the skilled person and may be used in the common amounts and are selected by the skilled person as they are required and according to the respective purpose for which the polyolefin compositions shall be used. Preferably (D) comprises an acid scavenger, preferably an inorganic based acid scavenger, and an antioxidant. Preferably, the amount of the antioxidant is at most 1500 ppm, for example at most 1000 ppm or at most 500 ppm, of the total composition.

Preferably, the composition is substantially free of nucleating agent or a clarifier. This advantageously makes the composition suitable for use in medical applications. For example, the composition comprises less than 1000 ppm, preferably less than 500 ppm, more preferably less than 250 ppm, most preferably less than 100 ppm of a nucleating agent or a clarifier with respect to the total composition.

For purpose of the invention with nucleating agent is meant any material that effectively accelerates the phase change from liquid polymer to semi-crystalline polymer (evident via faster crystallization rates measured with a differential scanning calorimeter or small crystallites observed with an optical microscope).

Further Aspects

The invention further relates to an article, preferably a film prepared from the composition according to the invention.

In another aspect, the invention relates to a medical article comprising the composition according to the invention or the film according to invention. Preferably, the medical article is chosen from the group of intravenous bags, intravenous tubes, intravenous bottles and dialysis bags.

Preferably, the medical article is a medical article suitable for sterilization at 121° C. or temperatures between 121° C. to 130° C. The suitability can be tested by measuring the concentration of certain ions after soluble testing. Low concentration of certain ions shows that the medical article is suitable for sterilization.

Concentration of Ions after Soluble Testing

The concentration of certain ions can be tested according to the following soluble test. Provide samples of 5 cm*0.5 cm, 200 micrometer and rinse by distilled water. After drying at room temperature, put the sample in a glass bottle of 500 ml and add 200 ml distilled water and make it hermetic. Then put the bottle in a high pressure vaporize sterilization device at 121° C. and heat for 30 minutes. Cool down to room temperature and use the solution for measuring the concentration of ions.

Each of the concentrations of Ba, Cu, Pb, Cr, Cd, Sn and Al ions in the solution can be tested for compliance with medical requirements.

Preferably, each of the concentrations of Ba, Cu, Pb and Cr ions is at most 1 ppm, more preferably at most 0.9 ppm, more preferably at most 0.8 ppm.

Preferably, each of the concentrations of Cd and Sn ions is at most 0.1 ppm, more preferably at most 0.09 ppm, more preferably at most 0.08 ppm.

Preferably, the concentration of Al ion is at most 0.05 ppm, more preferably at most 0.045 ppm, more preferably at most 0.04 ppm.

Accordingly the invention relates to a medical article wherein concentrations of Ba, Cu, Pb, Cr, Cd, Sn and Al ions in a solution obtained from a soluble test using a sample made of the composition according to the invention are measured to be:

each of the concentrations of Ba, Cu, Pb and Cr ions is at most 1 ppm, more preferably at most 0.9 ppm, more preferably at most 0.8 ppm, each of the concentrations of Cd and Sn ions is at most 0.1 ppm, more preferably at most 0.09 ppm, more preferably at most 0.08 ppm and the concentration of Al ion in the solution is at most 0.05 ppm, more preferably at most 0.045 ppm, more preferably at most 0.04 ppm, wherein the soluble test is performed by providing a sample of 5 cm*0.5 cm, 200 micrometer from the composition according to the invention, rinsing the sample by distilled water and drying at room temperature, putting the sample in a glass bottle of 500 ml and adding 200 ml distilled water and making it hermetic, putting the bottle in a high pressure vaporize sterilization device at 121° C. and heating for 30 minutes, cooling the bottle down to room temperature and measuring the concentrations of the ions of the solution in the glass bottle.

The invention further relates to use of the composition according to the invention or the film according to the invention for medical applications, for example intravenous bags, intravenous tubes, intravenous bottles and dialysis bags.

It is noted that the invention relates to all possible combinations of features described herein, preferred in particular are those combinations of features that are present in the claims. It will therefore be appreciated that all combinations of features relating to the composition according to the invention; all combinations of features relating to the process according to the invention and all combinations of features relating to the composition according to the invention and features relating to the process according to the invention are described herein.

It is further noted that the term 'comprising' does not exclude the presence of other elements. However, it is also to be understood that a description on a product/composition comprising certain components also discloses a product/composition consisting of these components. The product/composition consisting of these components may be advantageous in that it offers a simpler, more economical process for the preparation of the product/composition. Similarly, it is also to be understood that a description on a process comprising certain steps also discloses a process consisting of these steps. The process consisting of these steps may be advantageous in that it offers a simpler, more economical process.

The invention is now elucidated by way of the following examples, without however being limited thereto.

EXPERIMENTS

Components used in the experiments are summarized in Table 1. In all tables, all % means wt %, unless indicated otherwise.

TABLE 1

| Items | Description |
|---|---|
| (A) Propylene-ethylene copolymer | C3-C2 copolymer, MFR: 8 g/10 min @ 230 C./2.16 kg, C2%: 3.2%, XS %: 6.08% |
| (B) Terpolymer 1 | C3-C4-C2 terpolymer, C3%: 72.73%, C4%: 23%, C2%: 4.27%, MFR: 4 g/10 min @ 230 C./2.16 kg, Density: 0.868 g/cm3 |
| (B) Terpolymer 2 | C3-C4-C2 terpolymer, C3%: 72.65%, C4%: 20.75%, C2%: 6.6%, MFR: 6 g/10 min @ 230 C./2.16 kg, Density: 0.867 g/cm3 |
| (B) Terpolymer 3 | C3-C4-C2 terpolymer, C3%: 83.68%, C4%: 7.31%, C2%: 9.01%, MFR: 6 g/10 min @ 230 C./2.16 kg, Density: 0.868 g/cm3 |
| (B) Terpolymer 4 | C3-C4-C2 terpolymer, C3%: 83.47%, C4%: 7.82%, C2%: 8.71%, MFR: 30 g/10 min @ 230 C./2.16 kg, Density: 0.868 g/cm3 |
| (C) Ethylene-1-butylene copolymer 1 | C2-C4 copolymer, C4%: 19.5%, MFR: 6.7 g/10 min @ 230 C./2.16 kg, Density: 0.885 g/cm3 |
| (C) Ethylene-1-butylene copolymer 2 | C2-C4 copolymer, C4%: 25.94%, MFR: 6.7 g/10 min @ 230 C./2.16 kg, Density: 0.87 g/cm3 |

XS %=xylene soluble in wt %
C2%=ethylene content in wt %
C3%=propylene content in wt %
C4%=butylene content in wt %

Components as shown in Tables 2-4 were premixed together and then dosed into the twin-screw extruder through main feeder. The twin-screw extruder used is ZSK26mc with L/D 40 and screw diameter 26 mm. Melting temperature was 220° C. Shear rate was 400 rpm and output was 20 kg/hr.

After extrusion, the pellets were dried at 70° C. for 4 hrs before injection molding. All testing bars and plaques were molded by FANUC injection molding machine (S-2000i) with proper conditions. Properties of the samples were measured and are summarized in Tables 2-4.

Testing

MFR

MFR was tested according to ISO1133 with condition of 2.16 kg at 230° C. by Toyoseiki Semi-auto MFR F-W01.

Flexural Modulus

Flexural modulus was tested according to ISO178 at 23° C. by ZWICK Z005. Testing specimen is 80*10*4 mm and specimen was conditioned for 72 hr at 23±1° C. and at relative humidity of 50±5% before testing.

Transmittance

Transmittance was tested according to ISO13468 by BYK Haze Gard II. Thickness was 2 mm. Specimens were conditioned for 72 hr at 23±1° C. and at relative humidity of 50±5% before testing.

Haze

Haze was tested according to ISO14782 by BYK Haze Gard II. Thickness was 0.5 mm. Specimens were conditioned for 72 hr at 23±1° C. and at relative humidity of 50±5% before testing.

Notched Charpy Impact Strength

Impact strength was tested according to ISO179 at 23° C. by Toyoseiki Digital Impact DG-UB. Specimen dimension was 80*10*4 mm and specimens were conditioned for 72 hr at 23±1° C. and at relative humidity of 50±5% before testing.

NMR

Composition information of the elastomers was analyzed by NMR. All spectra were recorded on a Bruker AVANCE III HD 600 MHz digital NMR spectrometer equipped with PA BBO 600S3 BBF-H-D-05 Z SP Probe-head (Z114607). The temperature control, data acquisition and processing were performed with TOPSPIN 3.2 software.

50 mg sample was added into a 5 mm NMR tube with 0.6 mL relaxation solution (60 mM Cr(acac)$_3$ in TCE-d2 solution) to dissolve it under 150° C.; Pulse program: zgig (inverse gated pulse sequence); Recycle delay (d1): 10 sec; Number of scans (NS): 5000.

Xylene Soluble % of C3-C2 Copolymer

Xylene soluble was tested according to ISO16152.

TABLE 2

| | CEx 1 | CEx 2 | Ex 3 | CEx 4 | CEx 5 | Ex 6 | CEx 7 | CEx 8 | CEx 9 | CEx 10 |
|---|---|---|---|---|---|---|---|---|---|---|
| C3-C2 copolymer | 99.9 | 89.9 | 89.9 | 89.9 | 69.9 | 69.9 | 69.9 | 49.9 | 49.9 | 49.9 |

TABLE 2-continued

| | CEx 1 | CEx 2 | Ex 3 | CEx 4 | CEx 5 | Ex 6 | CEx 7 | CEx 8 | CEx 9 | CEx 10 |
|---|---|---|---|---|---|---|---|---|---|---|
| Terpolymer 1 Tafmer PN0040 | | 10 | 5 | | 30 | 15 | | 50 | 25 | |
| C2-C4 copolymer 1 Tafmer A4085s | | | 5 | 10 | | 15 | 30 | | 25 | 50 |
| Primary antioxidant | 0.05 | 0.05 | 0.05 | 0.05 | 0.05 | 0.05 | 0.05 | 0.05 | 0.05 | 0.05 |
| Secondary antioxidant | 0.05 | 0.05 | 0.05 | 0.05 | 0.05 | 0.05 | 0.05 | 0.05 | 0.05 | 0.05 |
| MFR | 9.6 | 9.7 | 9.5 | 10 | 7.6 | 8.6 | 9.4 | 8.1 | 7.9 | 8.2 |
| Haze | 35.6 | 25.6 | 33.5 | 19.9 | 10.3 | 8.4 | 11.5 | 7 | 7.7 | 8.9 |
| Tensile strength | 29.1 | 23 | 22.3 | 23.5 | 15.4 | 16.4 | 17.3 | 10.2 | 10.8 | 12 |
| Flex modulus | 1020 | 712 | 842 | 880 | 469 | 541 | 699 | 206 | 294 | 516 |
| Notched charpy 23° C. | 3.9 | 7.7 | 8.3 | 7.5 | 18.1 | 23.5 | 11.3 | 74.5 | 72 | 61.3 |

The effect of the addition of C3-C4-C2 terpolymer and/or C2-C4 copolymer is observed varying the amounts of the C3-C4-C2 terpolymer and C2-C4 copolymer added.

The addition of C3-C4-C2 terpolymer and/or C2-C4 copolymer to C3-C2 copolymer leads to an increase in the impact strength and a decrease in the haze.

When the total amount of the C3-C4-C2 terpolymer and the C2-C4 copolymer is 10 wt % (CEx 2, Ex 3, CEx 4) or 30 wt % (CEx 5, Ex 6, CEx 7), the impact strength is better when both C3-C4-C2 terpolymer and C2-C4 copolymer are added compared to when only C3-C4-C2 terpolymer or C2-C4 copolymer is added.

When the total amount of the C3-C4-C2 terpolymer and the C2-C4 copolymer is 50 wt % (CEx 8, CEx 9, CEx 10), no increase in the impact strength is observed when both C3-C4-C2 terpolymer and C2-C4 copolymer are added compared to when only C3-C4-C2 terpolymer or C2-C4 copolymer is added.

When the total amount of the C3-C4-C2 terpolymer and the C2-C4 copolymer is 30 wt % (CEx 5, Ex 6, CEx 7), haze is decreased by the combination of C3-C4-C2 terpolymer and C2-C4 copolymer, compared to when only one of the copolymers is added.

TABLE 3

| | CEx 1 | CEx 11 | Ex 12 | CEx 13 | CEx 14 | CEx 15 | Ex 16 | CEx 17 |
|---|---|---|---|---|---|---|---|---|
| C3-C2 copolymer | 99.9 | 69.9 | 69.9 | 69.9 | 69.9 | 69.9 | 69.9 | 69.9 |
| Terpolymer 2 Tafmer PN3560 | | 30 | 15 | | | | | |
| Terpolymer 3 Tafmer PN2060 | | | | 30 | 15 | | | |
| Terpolymer 4 Tafmer PN20300 | | | | | | 30 | 15 | |
| C2-C4 copolymer 1 Tafmer A4085s | | | 15 | | 15 | | 15 | 30 |
| Primary antioxidant | 0.05 | 0.05 | 0.05 | 0.05 | 0.05 | 0.05 | 0.05 | 0.05 |
| Secondary antioxidant | 0.05 | 0.05 | 0.05 | 0.05 | 0.05 | 0.05 | 0.05 | 0.05 |
| MFR | 9.6 | 10 | 9.7 | 10.2 | 9.6 | 15.8 | 12.1 | 9.4 |
| Haze | 35.6 | 16.8 | 10.3 | 13.4 | 12.1 | 9.5 | 11.1 | 11.5 |
| Tensile strength | 29.1 | 15.4 | 16.3 | 16.4 | 16.6 | 16.5 | 16.9 | 17.3 |
| Flex modulus | 1020 | 388 | 491 | 439 | 538 | 436 | 498 | 699 |
| Notched charpy 23° C. | 3.9 | 19 | 20.3 | 15 | 24 | 13 | 15.1 | 11.3 |

Using different types of C3-C4-C2 terpolymers, the effect of the addition of C3-C4-C2 terpolymer and/or C2-C4 copolymer is observed.

The impact strength is better when both C3-C4-C2 terpolymer and C2-C4 copolymer are added, compared to when only C3-C4-C2 terpolymer or C2-C4 copolymer is added.

When the terpolymer is terpolymer 2, haze is decreased by the combination of C3-C4-C2 terpolymer and C2-C4 copolymer, compared to when only one of the copolymers is added.

TABLE 4

| | CEx 5 | CEx 18 | CEx 19 |
|---|---|---|---|
| C3-C2 copolymer | 69.9 | 69.9 | 69.9 |
| Terpolymer 1 Tafmer PN0040 | 30 | 15 | |

TABLE 4-continued

|  | CEx 5 | CEx 18 | CEx 19 |
| --- | --- | --- | --- |
| C2-C4 Copolymer 2 Tafmer A4070s |  | 15 | 30 |
| Irganox1010 | 0.05 | 0.05 | 0.05 |
| Irgafos168 | 0.05 | 0.05 | 0.05 |
| MFR | 7.6 | 8.9 | 8.9 |
| Haze | 10.3 | 15.8 | 26.4 |
| Tensile strength | 15.4 | 15.7 | 16.3 |
| Flex modulus | 469 | 566 | 659 |
| Notched charpy 23° C. | 18.1 | 34.7 | 27.8 |

Using a different type of C2-C4 copolymer from Table 2, the effect of the addition of C3-C4-C2 terpolymer and/or C2-C4 copolymer is observed.

The impact strength is better when both C3-C4-C2 terpolymer and C2-C4 copolymer are added, compared to when only C3-C4-C2 terpolymer or C2-C4 copolymer is added.

Comparing Ex 6 versus CEx 18, the use of a higher density C2-C4 copolymer 1 (Ex 6) results in a much lower haze than the use of a lower density C2-C4 copolymer 2 (CEx 18) while the other properties are retained at acceptable levels.

The invention claimed is:

1. A composition comprising:
   (A) a propylene-based polymer which is a propylene homopolymer or a propylene copolymer consisting of at least 90 wt % of propylene monomer units and at most 10 wt % of ethylene monomer units and/or an α-olefin monomer units having 4 to 10 carbon atoms,
   (B) a terpolymer of propylene, an α-olefin having 4 to 10 carbon atoms and ethylene, wherein the amount of ethylene in the terpolymer (B) is 1 to less than 10 wt % with respect to the terpolymer (B), and
   (C) a copolymer of ethylene and an α-olefin having 4 to 10 carbon atoms, wherein the copolymer (C) has a density of at least 0.880 g/cm$^3$,
   wherein the amount of the propylene-based polymer (A) is at least 60 wt % with respect to the total composition.

2. The composition according to claim 1, wherein the amount of the propylene-based polymer (A) is 60 to 98 wt %, the amount of the terpolymer (B) is 1 to 30 wt % and the amount of the copolymer (C) is 1 to 30 wt %, with respect to the total composition.

3. The composition according to claim 1, wherein the propylene-based polymer (A) is a random propylene-ethylene copolymer consisting of 90-99 wt % of propylene monomer units and 1-10 wt % of ethylene monomer units.

4. The composition according to claim 1, wherein the terpolymer (B) is a terpolymer of propylene, 1-butene and ethylene.

5. The composition according to claim 1, wherein the amount of propylene in the terpolymer (B) is 70 to 90 wt % and the amount of the α-olefin in the terpolymer (B) is 5 to 30 wt %.

6. The composition according to claim 5, wherein the amount of the α-olefin in the terpolymer (B) is 15 to 30 wt % with respect to the terpolymer (B).

7. The composition according to claim 1, wherein the total amount of the terpolymer (B) and the copolymer (C) is 15 to 40 wt % with respect to the total composition and the weight ratio of the terpolymer (B) to the copolymer (C) is 0.5 to 4.

8. The composition according to claim 1, wherein the composition further comprises (D) additives, wherein the total of (A), (B), (C) and (D) is 100 wt % of the total composition and the amount of (D) is up to 5000 ppm of the total composition.

9. The composition according to claim 1, wherein the composition comprises less than 1000 ppm of a nucleating agent or a clarifier with respect to the total composition.

10. The composition according to claim 1, wherein concentrations of Ba, Cu, Pb, Cr, Cd, Sn and Al ions in a solution obtained from a soluble test using a sample made of the composition are measured to be:
   each of the concentrations of Ba, Cu, Pb and Cr ions is at most 1 ppm,
   each of the concentrations of Cd and Sn ions is at most 0.1 ppm, and
   the concentration of Al ion in the solution is at most 0.05 ppm,
   wherein the soluble test is performed by
      providing a sample of 5 cm*0.5 cm, 200 micrometer from the composition,
      rinsing the sample by distilled water and drying at room temperature,
      putting the sample in a glass bottle of 500 ml and adding 200 ml distilled water and making it hermetic,
      putting the bottle in a high pressure vaporize sterilization device at 121° C. and heating for 30 minutes,
      cooling the bottle down to room temperature, and
      measuring the concentrations of the ions of the solution in the glass bottle.

11. A film prepared from the composition according to claim 1.

12. A medical article comprising the composition according to claim 1.

13. The medical article according to claim 12, wherein the medical article is chosen from the group of intravenous bags, intravenous tubes, intravenous bottles, and dialysis bags.

14. The composition according to claim 1, wherein the amount of the propylene-based polymer (A) is 60 to 98 wt %, the amount of the terpolymer (B) is 1 to 30 wt % and the amount of the copolymer (C) is 1 to 30 wt %, with respect to the total composition,
   wherein the propylene-based polymer (A) is a random propylene-ethylene copolymer consisting of 90-99 wt % of propylene monomer units and 1-10 wt % of ethylene monomer units, wherein the amount of propylene in the terpolymer (B) is 70 to 90 wt %, the amount of the α-olefin in the terpolymer (B) is 5 to 30 wt % and the amount of ethylene in the terpolymer (B) is 1 to 10 wt %, with respect to the terpolymer (B),
   wherein the total amount of the terpolymer (B) and the copolymer (C) is 15 to 40 wt % with respect to the total composition and the weight ratio of the terpolymer (B) to the copolymer (C) is 1 to 3.5, and
   wherein the composition further comprises (D) additives, wherein the total of (A), (B), (C) and (D) is 100 wt % of the total composition and the amount of (D) is up to 5000 ppm of the total composition, and wherein (D) comprises an acid scavenger.

15. The composition according to claim 13, wherein the composition comprises less than 500 ppm of a nucleating agent or a clarifier with respect to the total composition.

16. The composition according to claim 14, wherein (D) comprises an inorganic based acid scavenger and an antioxidant.

17. The composition according to claim 1, wherein the amount of propylene-based polymer (A) is 60 to 90 wt %, the amount of the terpolymer (B) is 5 to 20 wt % and the amount of the copolymer (C) is 5 to 20 wt %, with respect to the total composition.

18. The composition according to claim 1, wherein the composition comprises less than 100 ppm of a nucleating agent or a clarifier with respect to the total composition.

19. The composition according to claim 10, wherein:
each of the concentrations of Ba, Cu, Pb and Cr ions is at most 0.9 ppm,
each of the concentrations of Cd and Sn ions is at most 0.09 ppm, and
the concentration of Al ion in the solution is at most 0.045 ppm.

20. A composition comprising:
(A) 75 to 90 wt % of a propylene-based polymer which is a propylene copolymer consisting of at least 90 wt % of propylene monomer units and at most 10 wt % of ethylene monomer units and/or an α-olefin monomer units having 4 to 10 carbon atoms,
(B) 5 to 20 wt % a terpolymer of propylene, an α-olefin having 4 carbon atoms and ethylene, wherein the amount of propylene in the terpolymer (B) is 70 to 90 wt %, the amount of the α-olefin in the terpolymer (B) is 5 to 30 wt %, and the amount of ethylene in the terpolymer (B) is 1 to 10 wt %, with respect to the terpolymer (B), and
(C) 5 to 20 wt % a copolymer of ethylene and an α-olefin having 4 carbon atoms, wherein the copolymer (C) has a density of at least 0.880 g/cm$^3$,
wherein the amounts are with respect to the total composition.

* * * * *